United States Patent
Russ

(10) Patent No.: US 6,749,566 B2
(45) Date of Patent: Jun. 15, 2004

(54) PATIENT MONITORING AREA NETWORK

(75) Inventor: Tomas Russ, Carlisle, MA (US)

(73) Assignee: Draeger Medical Systems, Inc., Danvers, MA (US)

(*) Notice: Subject to any disclaimer, the term of this patent is extended or adjusted under 35 U.S.C. 154(b) by 17 days.

(21) Appl. No.: 10/075,674

(22) Filed: Feb. 13, 2002

(65) Prior Publication Data

US 2002/0115914 A1 Aug. 22, 2002

Related U.S. Application Data

(60) Provisional application No. 60/268,770, filed on Feb. 14, 2001.

(51) Int. Cl.$^7$ ................................................. A61B 5/00
(52) U.S. Cl. ......................... 600/300; 128/903; 128/904
(58) Field of Search ................................ 600/300, 301, 600/483–484, 490, 508–509, 555; 128/903–904, 920–921; 705/2–4; 340/573.1–573.4, 538–539; 379/106.1–106.2, 38; 607/28–32, 59–60; 702/200, 208–211, 100; 455/418–419, 423

(56) References Cited

U.S. PATENT DOCUMENTS

| | | | |
|---|---|---|---|
| 5,375,604 A | 12/1994 | Kelly et al. | 600/484 |
| 5,417,222 A | 5/1995 | Dempsey et al. | 600/509 |
| 5,458,123 A | 10/1995 | Unger | 600/509 |
| 5,544,649 A | 8/1996 | David et al. | 600/301 |
| 5,544,661 A | 8/1996 | Davis et al. | 600/513 |
| 5,564,429 A | 10/1996 | Bornn et al. | 600/508 |
| 5,579,001 A | 11/1996 | Dempsey et al. | 340/870.01 |
| 5,579,775 A | 12/1996 | Dempsey et al. | 600/483 |
| 5,673,692 A | 10/1997 | Schulze et al. | 600/301 |
| 5,704,351 A | 1/1998 | Mortara et al. | 600/509 |
| 5,752,917 A | 5/1998 | Fuchs | 600/484 |

(List continued on next page.)

FOREIGN PATENT DOCUMENTS

| | | |
|---|---|---|
| EP | 1 062 906 A1 | 12/2000 |
| WO | WO 99/44494 | 9/1999 |
| WO | WO 00/36900 | 6/2000 |
| WO | WO 00/62664 | 10/2000 |
| WO | WO 01/80731 | 11/2001 |

OTHER PUBLICATIONS

Harry Newton, "Newton's Telecom Dictionary", Feb. 2002, CMP Books, 18$^{th}$ edition, p. 104 and 569.*

John Lortz and Susan Leavitt, "What is Bluetooth? We Explain The Newest Short–Range Connectivity Technology" 2002, Sandhill Publishing, Smart Computing Learning Series Wireless Computing, pp. 72–74.*

Ron White, "How Computers Work" Sep. 2001, Que Corporation, 6th Edition, p. 327.*

Primary Examiner—Max F. Hindenburg
Assistant Examiner—Michael Astorino
(74) Attorney, Agent, or Firm—Jack Schwartz & Associates

(57) ABSTRACT

A system that allows patient monitoring data obtained by patient connected devices to be transferred by wireless signals to another device such as a patient monitoring processor. The same patient connected devices are used to transfer data to the patient monitor processor or a central station depending on the location of the patient. A single device is used for both a personal area network and a telemetry/transport application. The same wireless technology is used in both situations and eliminates the need to deploy more than one antenna/receiver system. Existing wireless transfer protocols such as Bluetooth are used, thereby reducing transmission power when the two communicating devices are in close proximity.

22 Claims, 3 Drawing Sheets

U.S. PATENT DOCUMENTS

| | | | |
|---|---|---|---|
| 5,752,976 A | 5/1998 | Duffin et al. | 607/32 |
| 5,755,230 A | 5/1998 | Schmidt et al. | 600/594 |
| 5,882,300 A | 3/1999 | Malinouskas et al. | 600/300 |
| 5,919,141 A | 7/1999 | Money et al. | 600/513 |
| 5,931,791 A | 8/1999 | Saltzstein et al. | 600/513 |
| 5,944,659 A | 8/1999 | Flach et al. | 600/300 |
| 5,949,777 A | 9/1999 | Uyesugi et al. | 370/345 |
| 5,963,130 A | 10/1999 | Schlager et al. | 340/540 |
| 6,017,315 A | 1/2000 | Starr et al. | 600/538 |
| 6,024,699 A | 2/2000 | Surwit et al. | 600/300 |
| 6,052,614 A | 4/2000 | Morris, Sr. et al. | 600/509 |
| 6,052,615 A | 4/2000 | Feild et al. | 600/509 |
| 6,083,248 A | 7/2000 | Thompson | 607/30 |
| 6,093,146 A | 7/2000 | Filangeri | 600/300 |
| 6,167,258 A | 12/2000 | Schmidt et al. | 455/419 |
| 6,198,390 B1 | 3/2001 | Schlager et al. | 340/540 |
| 6,213,942 B1 | 4/2001 | Flach et al. | 600/300 |
| 6,221,012 B1 | 4/2001 | Maschke et al. | 600/301 |
| 6,230,049 B1 | 5/2001 | Fischell et al. | 600/544 |
| 6,249,705 B1 | 6/2001 | Snell | 607/59 |
| 6,252,883 B1 | 6/2001 | Schweickart et al. | 370/441 |
| 6,292,698 B1 | 9/2001 | Duffin et al. | 607/32 |
| 6,294,999 B1 * | 9/2001 | Yarin et al. | 340/573.1 |
| 6,315,719 B1 | 11/2001 | Rode et al. | 600/300 |
| 6,342,040 B1 | 1/2002 | Starr et al. | 600/538 |
| 6,396,416 B1 | 5/2002 | Kuusela et al. | 340/870.28 |
| 6,416,471 B1 | 7/2002 | Kumar et al. | 600/300 |
| 6,440,068 B1 * | 8/2002 | Brown et al. | 600/300 |
| 6,443,906 B1 * | 9/2002 | Ting et al. | 600/490 |
| 6,471,645 B1 * | 10/2002 | Warkentin et al. | 600/300 |
| 6,544,173 B2 | 4/2003 | West et al. | 600/300 |
| 6,544,174 B2 | 4/2003 | West et al. | 600/300 |
| 2001/0034475 A1 | 10/2001 | Flach et al. | 600/300 |
| 2001/0049470 A1 | 12/2001 | Mault et al. | 600/300 |
| 2001/0056226 A1 | 12/2001 | Zodnik et al. | 600/300 |
| 2002/0000916 A1 | 1/2002 | Richards | 340/539 |
| 2002/0013517 A1 | 1/2002 | West et al. | 600/300 |
| 2002/0013518 A1 | 1/2002 | West et al. | 600/300 |
| 2002/0013614 A1 | 1/2002 | Thompson | 607/60 |

* cited by examiner

PATIENT MONITORING AREA NETWORK

This application is based on provisional patent application No. 60/268,770 filed on Feb. 14, 2001.

FIELD OF THE INVENTION

This invention relates generally to the field of medical devices and more particularly to a wireless data gathering and transmission system to be used with patients receiving treatment in a hospital.

BACKGROUND OF THE INVENTION

In a typical patient monitoring environment several electrodes or sensors are attached to a patient and then connected through wires to a Patient Monitor Processor as depicted in FIG. 1. In an operating room, for example, wires from five, six or ten electrocardiogram (EKG) electrodes, an SpO2 sensor, a CO2 sensor, one, two or four pressure transducers, a pressure cuff, one or more temperature transducers and EEG electrodes may have to be connected between the patient and the Patient Monitoring Processor. This presents a particularly complex cable management problem for the attending physician or nurse. Considerable time can be consumed in disentangling the patient when they must be disconnected or transferred to another area of the hospital. Ideally, a reduction or elimination of all of the cable connections between the patient and the Patient Monitor Processor could be achieved. This could be effectively accomplished by the use of two way wireless transmission and reception between one or more Patient Connected Devices and the Patient Monitor Processor while using the same underlying wireless technology.

Wireless data acquisition systems are well known in the biomedical area. For example, U.S. Pat. No. 5,704,351 issued to Mortara discloses a multiple channel biomedical digital telemetry transmitter. Mortara teaches an eight channel biomedical transmitter specifically directed to an electrocardiogram (EKG) signal transmission in the 902 to 928 MHz band. The Mortara device includes input circuitry and an analog to digital converter which receives the input signal from an EKG electrode and converts it to a digital signal which is inputted to a microprocessor. The microprocessor then converts the digital signal to a serial digital output signal which is used to frequency modulate the radio frequency carrier signal for telemetry transmission. The carrier frequency is adjustable within the 902 to 928 MHz band by two manual frequency setting switches. The use of these manual switches is the only adjustment available on the Mortara device and is capable only of manually setting the specific frequency within the 902 to 928 MHz band. The input circuitry and analog to digital converter are not adjustable or adaptable to accept different input signal characteristics. Further, the Mortara device cannot be adjusted by programming or otherwise to operate in any other frequency band. Finally, the Mortara device is only a transmitter and is unable to receive RF or other signals to control its operation.

Similarly, U.S. Pat. No. 5,755,230, issued to Schmidt et al. discloses a device for monitoring a physiological signal, in particular an EEG, and transmitting the signal by RF to a receiver. Like Mortara, the Schmidt et al. device cannot be modified or adjusted to receive inputs from different physiological sensors.

U.S. Pat. No. 5,579,775, entitled DYNAMIC CONTROL OF A PATIENT MONITORING SYSTEM, issued to Dempsey discloses a patient monitoring system with a telemetry subsystem which monitors and transmits an RF signal representing the signals it receives from one or more physiological monitoring instruments. Unlike Mortara and Schmidt et al., Dempsey teaches a receiving subsystem which can receive RF signals in a backchannel arrangement in order to control the operation of the system. However, Dempsey does not include the capability to adjust or modify the input by programming or otherwise in response to different physiological signals. The device relies on separate monitoring sections in order to accommodate different physiological signals such as EEG, EKG and SpO2.

U.S. Pat. No. 5,417,222, also issued to Dempsey, discloses a portable processor which may be interconnected to a telemetry monitor at the I/O port. The Dempsey '222 device includes a telemetry monitor comprising a physiological monitor which receives selected physiological signals indicating a specific physiological condition of the patient. The physiological monitor is a specific type of monitor that reads signals of a specific physiological function such as EKG, for example. In the event that a different physiological function is to be monitored such as EEG a different physiological monitor must be employed. In particular, Dempsey '222 discloses the interface of a programmable processor (the Hewlett Packard 100LX palmtop processor) with a physiological monitor. The device is not able to adapt or change the physiological monitor, by software or otherwise, to accept different physiological signals.

The Fluke corporation manufactures a wireless data acquisition system under the trade name of "Wireless Logger". The "Wireless Logger" is an integration of Fluke's Hydra Data Logger, a portable instrument monitor/analyzer, which accepts wired external inputs, with an RF modem. The Hydra Data Logger includes a universal input module which accepts and conditions external inputs. The resulting signals are transmitted by the modem to another modem interconnected to a personal computer. The separate modem and universal input module are relatively large and consume up to ten watts of power. The operation of the system is not software programmable. RF Neulink markets a similar system utilizing the VHF (136–280 MHz) and UHF (403–512 MHz) bands.

U.S. Pat. No. 6,167,258, entitled PROGRAMMABLE WIRELESS DATA ACQUISITION SYSTEM, issued to Schmidt et al, discloses the use of a signal processing module which is capable of accepting multiple external inputs having different characteristics and ranges. The '258 Schmidt et al. device, through programming, converts and conditions the external inputs, generates an RF signal encoded with data corresponding to the external inputs and transmits the signal to a base station.

U.S. Pat. No. 6,230,049, entitled INTEGRATED SYSTEM FOR EEG MONITORING AND ELECTRICAL STIMULATION WITH A MULTIPLICITY OF ELECTRODES, issued to Fischell et al., discloses an integrated EEG monitoring and electrical stimulation system that has a wireless link between a patient electronics module and an EEG analysis workstation.

In general, the prior art attempts at monitoring and transferring patient data are illustrated in FIGS. 1 and 3. In none of these cases is the same patient connected device used to transfer data to either a patient monitor processor or a central station with the same underlying wireless technology. Accordingly, a need remains for a system based on the same underlying technology that allows patient monitoring data collected by multiple monitors connected to a patient to be wirelessly transferred to another device such as a Patient Monitoring Processor for the purpose of displaying, synchronizing and processing the data.

SUMMARY OF THE INVENTION

The present invention is a system that allows patient monitoring data collected by one or more sensors or devices connected to a patient to be wirelessly transferred to another device, such as a patient monitoring processor. The transferred data may be displayed, synchronized and otherwise processed. The patient monitoring processor may be located in close proximity to the patient or at some distance depending on the mode of operation of the patient monitoring system. The wireless data transfer operates in both directions, that is, data can also be transferred from the patient monitor processor to the patient connected devices. The same patient connected device is used to transfer and receive data to or from either a patient monitor processor, a central station or both depending on the state of the patient without any alteration of the patient connected device hardware.

DETAILED DESCRIPTION OF THE INVENTION

Figure 1:
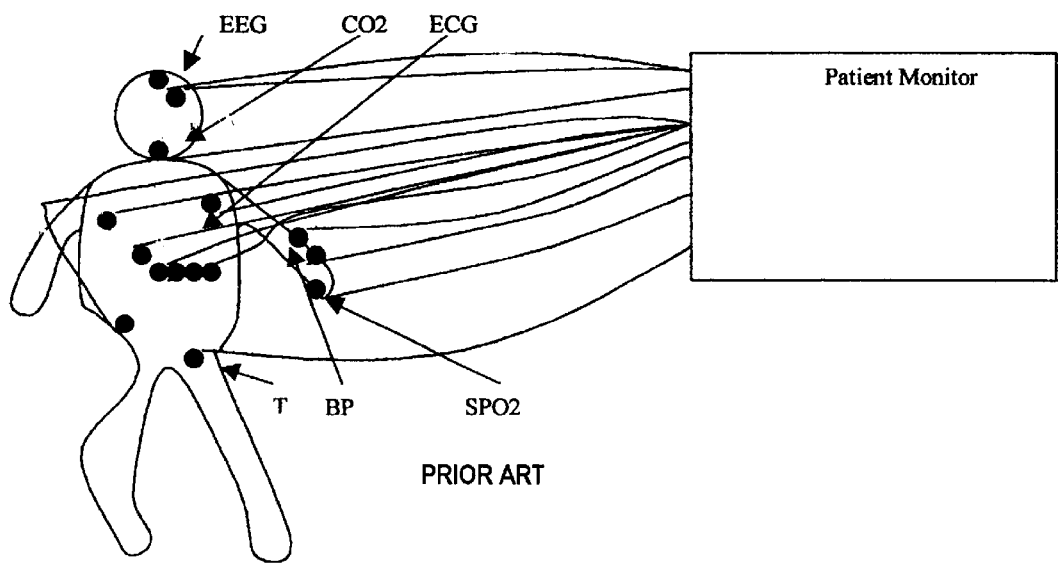
FIG. 1 is a schematic diagram of a prior art system for monitoring a patient.
Figure 2:
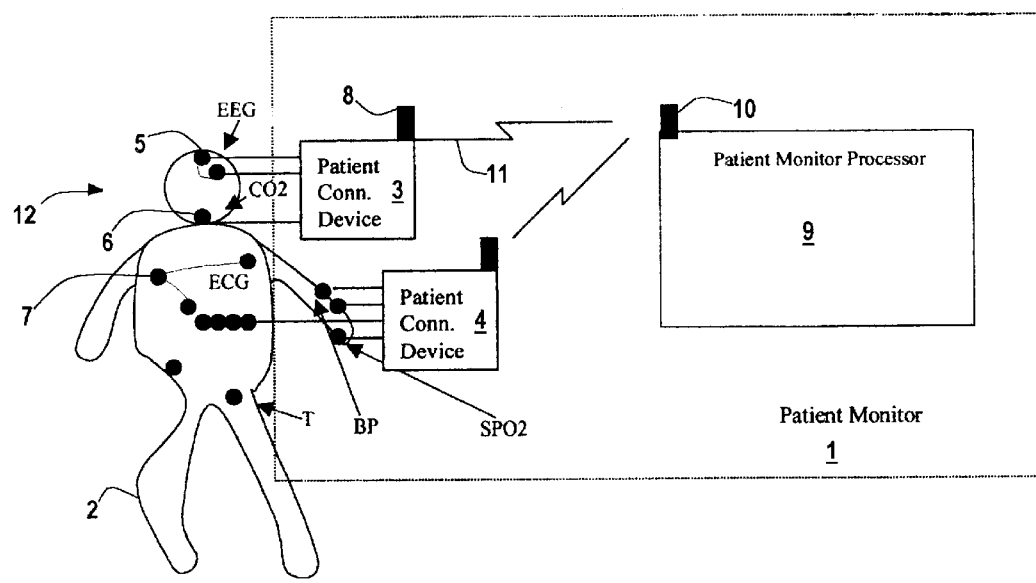
FIG. 2 is a schematic diagram of a patient monitoring system constructed according to the principles of the present invention.
Figure 3:
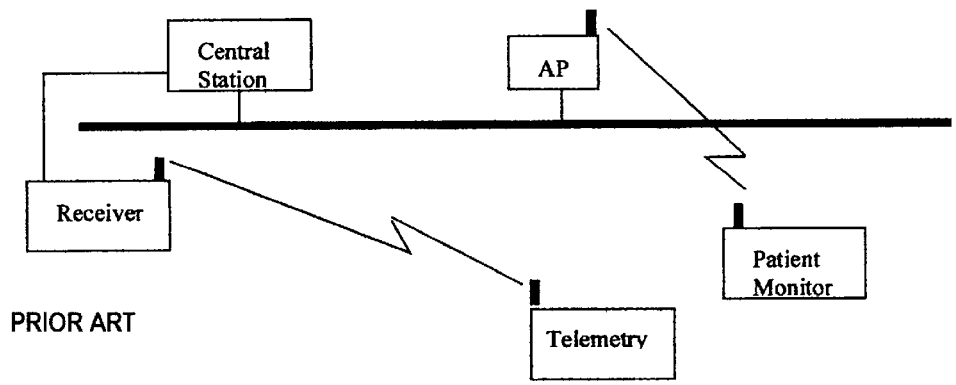
FIG. 3 is a schematic diagram of a prior art patient monitoring telemetry system.

Referring to FIG. 2, a two way wireless patient monitoring system is shown generally at 1. The patient 2 is attached to a plurality of patient connected devices 3 and 4. Patient connected device 3, for example, contains an EEG sensor 5, carbon dioxide monitor 6 and an ECG sensor 7. Each sensor 5, 6 and 7 is interconnected to a common device 3 which contains suitable data gathering electronics as well as an RF transceiver interconnected to antenna 8. Also contained within the common device 3 is microprocessor which enables the device 3 to function as a slave station in a piconet. Patient connected device 4 operates in a manner similar to patient connected device 3.

A patient monitoring processor 9 includes a microprocessor and RF transceiver which is interconnected to antenna 10. Signals 11 are transferred between the patient connected device 3 and the patient monitoring processor 9 which can act as either a master or slave station within a wireless cell without any change of the patient monitoring processor hardware. The wireless data is transferred using any suitable protocol of which the Bluetooth standard is an example. Bluetooth technology provides a universal radio interface in the 2.45 GHz frequency band that enables portable electronic devices to connect and communicate wirelessly via short range ad hoc networks.

Bluetooth technology is described for example in Haartsen, "Bluetooth, The Universal Radio Interface for Ad Hoc, Wireless Connectivity", Ericsson Review No. 3, 1998, pp. 110–117. A wireless cell or "piconet" composed of the patient monitoring processor 9 acting in this case as the master station and the patient connected devices 3 and 4 acting as slave stations permits the transfer of physiological data from any of the patient connected devices 3 and 4 to the patient monitoring processor 9 for the purpose of displaying data, interpreting data and synchronizing the operation of the several patient connected devices. This architecture creates a personal area network 12.

Figure 4:
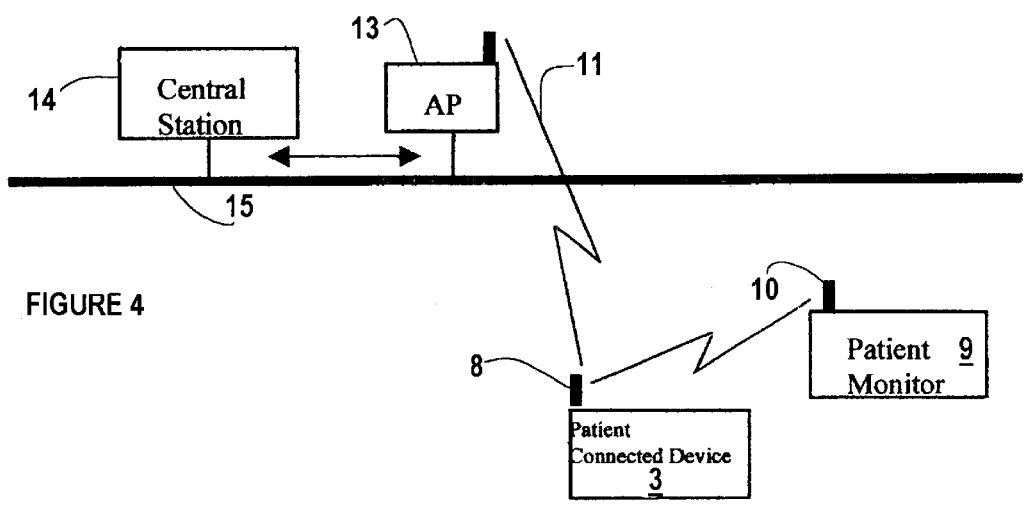
FIG. 4 is a schematic diagram of wireless patient monitoring system constructed according to the principles of the present invention.

Referring also to FIG. 4, the same patient connected devices 3 and 4 (device 4 not shown) are also able to transfer data to a device other than the patient monitor processor 9. In particular, there will be instances where the patient 2 is being transferred from one area to another or perhaps is well enough to be able to walk around the area on her own. In those instances there would still be a desire to monitor the patient from a distance. The patient connected device 3 can transmit the data signal 11 to the patient monitor 9, but can also simultaneously or serially (consecutively) transmit the data signal 11 to an auxiliary processor 13, depending on the location of the patient 2. The auxiliary processor 13 is interconnected to a central station 14 by a conventional network 15.

Figure 5:
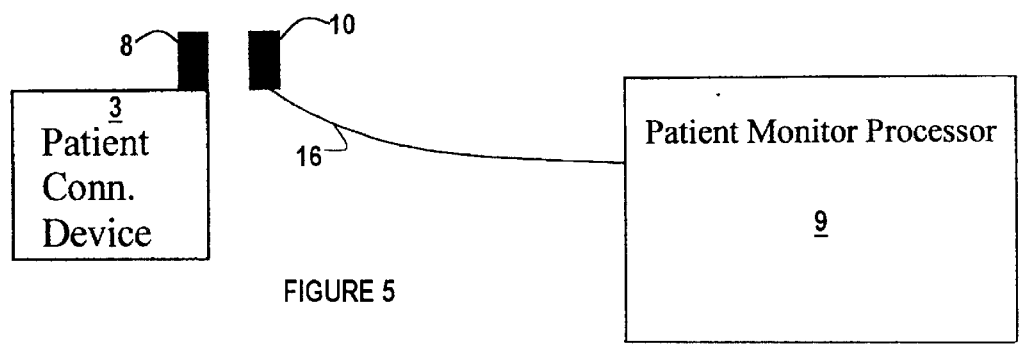
FIG. 5 is a schematic diagram of an antenna arrangement used in the system depicted in FIG. 2.

Referring also to FIG. 5, the power of the wireless transceiver housed within the patient connected device 3 can be adjusted to minimize interference with other piconets in the area, and to minimize the number of receiving stations when transferring telemetry. Existing Bluetooth specifications are designed to reduce transmission power when the two communicating devices are in close proximity. The benefit of reduced power consumption is to extend battery life of the patient connected device 3 and to reduce the likelihood of interference with other nearby wireless devices. Ideally the antennae of both communicating devices should be as close together as possible. The Bluetooth master antenna 10 which is connected to the patient monitor processor 9 is located at the end of an extension cable 16 in order to reduce the distance to the antenna 8 of patient connected device 3.

Figure 6:
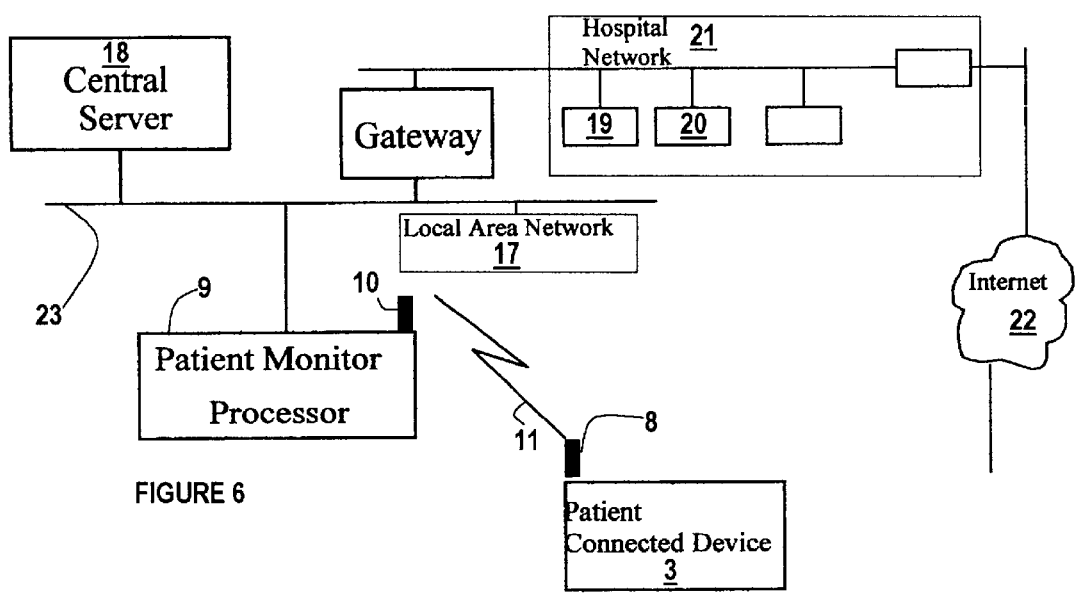
FIG. 6 a schematic diagram of a patient monitoring processor subsystem as utilized in the system depicted in FIG. 2.

The present system 12 separates the physiological signal acquisition (obtained via patient connected devices 3 and 4) from the backend processing and display of the signals accomplished by the patient monitor processor 9. Referring also to FIG. 6, the patient monitor processor 9 is a standard workstation or web browser device. The patient monitor processor 9 is connected to a local area network 17 and performs functions not only as the local display for patient monitoring but also retrieves other useful information for the physician who may reside elsewhere. Such information for example is contained in a central database server 18 on the local area network 17, or the information may be contained in other places 19, 20 in the overall hospital network 21. Information may also be obtained from the internet 22. The patient monitor processor 9 may be used as a local display and also as a window into other medical and nonmedical information accessible through the network connection 23.

I claim:

1. A patient area network, comprising:
   (a) at least two patient connected devices, each of the at least two patient connected devices comprising
      a sensor adapted to detect and store at least one physiological parameter from a patient; and
      a radio frequency transceiver adapted to communicate with a patient monitor processor; and
   (b) the patient monitor processor adapted to receive wireless physiological data from the at least two patient connected devices and to transmit wireless instructions to the at least two patient connected devices, the patient monitor processor being configured to act as one of (i) a master station within a cell and (ii) a slave station within a cell;
wherein the patient monitor processor is configured to:
display physiological data received from each of the at least two patient connected devices;
interpret physiological data received from each of the at least two patient connected devices; and
synchronize operation of each of the at least two patient connected devices with other of the at least two patient connected devices.

2. The patient area network of claim 1 further comprising a central station adapted to send and receive data from each patient connected device.

3. The patient area network of claim 2 wherein the central station further comprises: a radio frequency transceiver configured to communicate with each patient connected device.

4. The patient area network of claim 3 further comprising a wireless data transfer protocol adapted to reduce transmission power in response to close proximity of a patient connected device to any data receiving device within the cell.

5. The patient area network of claim 4 further comprising:
a master antenna; and
an extension cable interconnecting the master antenna and the patient monitor processor configured to decrease separation between the patient connected device and the patient monitor processor.

6. The patient area network of claim 5 wherein the patient monitor processor comprises a web browser.

7. The patient area network of claim 6 wherein the patient monitor processor is interconnected to a local area network.

8. The patient area network of claim 7 wherein the local area network comprises an internet connection.

9. A method of monitoring physiological signs from a patient, comprising the steps of:
using at least one physiological parameter sensor adapted to be attached to a patient;
interconnecting the physiological parameter sensor to a first wireless transceiver;
transmitting a physiological data signal from the first wireless transceiver to a patient monitor processor;
interconnecting the patient monitor processor to a second wireless transceiver;
transmitting informational data from the second wireless transceiver to the first wireless transceiver; and
designating the patient monitor processor as one of(a) a master station in a wireless cell and (b) a slave station in a wireless cell:
wherein the patient monitor processor performs the steps of
displaying physiological data received from each patient connected device;
interpreting physiological data received from each patient connected device; and
synchronizing operation of each patient connected device with other patient connected devices.

10. The method of claim 9, further comprising the steps of:
interconnecting an auxiliary processor to a central station;
transmitting data from the first wireless transceiver to the auxiliary processor; and
transmitting data from the auxiliary processor to the first wireless transceiver.

11. The method of claim 10 further comprising the step of communicating between the first wireless transceiver and the auxiliary processor by means of a wireless protocol that reduces transmission power as path length between the first wireless transceiver and the auxiliary processor decreases.

12. The method of claim 11, further comprising the step of interconnecting an antenna to the second wireless transceiver by means of an extension cable so as to decrease the path length between the antenna and the first wireless transceiver.

13. The method of claim 12, further comprising the step of configuring the patient monitor processor as a web browser.

14. The method of claim 13 further comprising the step of interconnecting the patient monitor processor to a local area network.

15. The method of claim 14 further comprising the step of linking the local area network to an internet connection.

16. A method of monitoring physiological signals from a patient, comprising the steps of:
using at least one physiological parameter sensor adapted to be attached to a patient;
interconnecting the physiological parameter sensor to a first wireless transceiver of a patient connected device;
adaptively conditioning a physiological data signal for at least one of, (a) an ambulatory patient mode and (b) a non-ambulatory patient mode;
designating a patient monitor processor as one of (a) a master station in a wireless cell and (b) a slave station in a wireless cell; and
transmitting said physiological data signal from the first wireless transceiver to the patient monitor processor, which is adapted to receive wireless physiological data from the patient connected device and to transmit wireless instructions to the patient.

17. The method of claim 16 further comprising the step of adaptively selecting between said ambulatory patient mode and said non-ambulatory patient mode in response to user command.

18. The method of claim 16 wherein said transmitting step uses a single transmitter for both said ambulatory patient mode and said non-ambulatory patient mode.

19. The method of claim 16 further comprising the steps of:
using a plurality of physiological parameter sensors of different type attached to a patient;
interconnecting said physiological parameter sensors to at least one wireless transceiver;
adaptively conditioning physiological data signals containing different types of physiological data for at least one of, (a) an ambulatory patient mode and (b) a non-ambulatory patient mode; and
transmitting said physiological data signals from said at least one wireless transceiver to a patient monitor processor.

20. The method of claim 19 including the step of using a map for dynamically allocating said physiological data signals to corresponding ports on said at least one transceiver.

21. The method of claim 19 wherein said different types of physiological data include at least two of, (a) EKG/ECG data, (b) EEG data, (c) blood pressure data, (d) respiratory data, (e) blood parameter data, (f) pulse rate data and (g) muscle activity associated data.

22. A patient area network, comprising:
(a) a plurality of patient connected devices, each of said plurality of patient connected devices comprising:
   (i) at least one sensor adapted to detect and store at least one physiological parameter from a patient; and
   (ii) a radio frequency transceiver;
(b) a plurality of patient monitor processors adapted to receive wireless physiological data from the radio frequency transceiver of each of the plurality of patient connected devices and to transmit wireless instructions to each of the plurality of patient connected devices, each of the plurality of patient monitor processors being configured to act as one of:
   (i) a master station within a cell; and
   (ii) a slave station within a cell;
(c) a plurality of auxiliary processors adapted to receive wireless physiological data from each of the plurality of patient connected devices and to transmit wireless instructions to each of the plurality of patient connected devices, said plurality of auxiliary processors each being configured to act as one of
   (i) a master station within a cell; and
   (ii) a slave station within a cell;
(d) a central database server connected to said plurality of auxiliary data processors for receiving physiological data therefrom, said central database server including:
   (i) means for receiving physiological data from said plurality of patient connected devices and said plurality of patient monitor processors;
   (ii) means for storing said received physiological data; and
   (iii) means for continuously receiving, storing, and synchronizing physiological data derived from a respective patient connected device operating in any of (a) an ambulatory patient mode and (b) non-ambulatory patient mode.

* * * * *